United States Patent [19]

Clemens

[11] Patent Number: 4,496,747

[45] Date of Patent: Jan. 29, 1985

[54] PROCESS FOR THE PREPARATION OF DEHYDROACETIC ACID

[75] Inventor: Robert J. Clemens, Kingsport, Tenn.

[73] Assignee: Eastman Kodak Company, Rochester, N.Y.

[21] Appl. No.: 487,396

[22] Filed: Apr. 21, 1983

[51] Int. Cl.$^3$ ............................................ C07D 309/38
[52] U.S. Cl. .................................................. 549/291
[58] Field of Search ........................................ 549/291

[56] References Cited

U.S. PATENT DOCUMENTS

| | | | |
|---|---|---|---|
| 2,229,204 | 1/1941 | Boese | 549/291 |
| 2,849,456 | 8/1958 | Branch | 549/291 |
| 2,912,441 | 11/1959 | Montagna et al. | 549/291 |
| 3,336,339 | 8/1967 | England | 549/291 |
| 3,483,224 | 12/1969 | Fitzpatrick et al. | 549/291 |
| 3,493,586 | 2/1970 | Kuhn et al. | 549/291 |
| 3,592,826 | 7/1971 | Marcus et al. | 549/291 |

OTHER PUBLICATIONS

M. F. Carroll et al., Jour. Am. Chem. Soc., (1953), vol. 75, pp. 5400–5402.

*Primary Examiner*—Norma S. Milestone
*Attorney, Agent, or Firm*—Clyde L. Tootle; Gary C. Bailey; Daniel B. Reece, III

[57] ABSTRACT

A process for the preparation of dehydroacetic acid which comprises heating 2,2,6-trimethyl-4H-1,3-dioxin-4-one, preferably at a temperature of about 130° C. to about 160°C., the heating being carried out preferably in the presence of an inert solvent such as xylene and preferably dehydroacetic acid; the solvent being present in an amount of about 0.05 to about 2.0 moles per mole of the compound being heated, the process further comprising recovering dehydroacetic acid so produced.

8 Claims, No Drawings

PROCESS FOR THE PREPARATION OF DEHYDROACETIC ACID

BACKGROUND OF THE INVENTION

This invention relates to a novel process for the preparation of dehydroacetic acid, a compound useful as a fungicide, bactericide, and plasticizer as well as an intermediate in organic syntheses.

Dehydroacetic acid has been prepared by a variety of methods, many of which are based on the dimerization of diketene, generally at elevated temperatures and in the presence of a catalyst [See U.S. Pat. Nos. 2,229,204, 2,849,456 and 3,483,224]. Additionally, F. Arndt, *Organic Syntheses*, Coll. Vol. III, 1955, 231–233, reports the preparation of dehydroacetic acid by the condensation of ethyl acetoacetate in the presence of sodium bicarbonate at a temperature of 200° to 210° C. Disclosed by Carroll and Bader in the "Journal of American Chemical Society," Vol. 75, 5400–02, 1953, is the preparation of dehydroacetic acid in 51% yield by heating 2,2,6-trimethyl-4H-1,3-dioxin-4-one in toluene in the presence of calcium acetate for 5 hours.

According to the present invention, dehydroacetic acid is obtained in excellent yield, in short reaction time and with a minimum of reagents. The process of my invention begins not with the diketene as in many existing methods but with the compound 2,2,6-trimethyl-4H-1,3-dioxin-4-one, having the formula

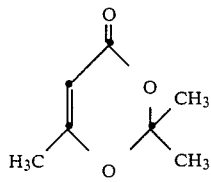

Surprisingly, I have found that dehydroacetic acid can be produced in nearly quantitative yields (up to about 99% yield) simply by heating compound I.

SUMMARY OF THE INVENTION

The present invention concerns the preparation of dehydroacetic acid. The process comprises heating 2,2,6-trimethyl-4H-1,3-dioxin-4-one and recovering the dehydroacetic acid produced therefrom.

DETAILED DESCRIPTION OF THE INVENTION

The process of my invention involves heating compound I to a sufficiently elevated temperature to pyrolyze compound I and yield the desired dehydroacetic acid. Compound I is a known compound and can be prepared according to the method disclosed by Carroll et al cited hereinabove, i.e. by reacting acetone and diketene in the presence of p-toluenesulfonic acid under reflux conditions.

The range of temperatures which may be employed in my process can be widely varied. While conversion of compound I to dehydroacetic acid can be achieved employing only slightly elevated temperatures, e.g. as low as about 80° C., the rate of the conversion at this low temperature becomes undesirably slow. Thus, a minimum temperature which will normally be employed is about 120° C. There generally are no restrictions on the upper limit of the temperature range except those dictated by equipment, economy and convenience. However, there is no particular advantage in carrying out the process of my invention at excessively high temperatures. Normally temperatures up to about 200° C. are sufficient. The preferred temperature range for my process is about 130° C. to about 160° C. Within this preferred temperature range the conversion of compound I to dehydroacetic acid is normally achieved in a minimum of reaction time and in excellent yield. On a laboratory scale, such as disclosed in the experimental examples set out herein, conversion of compound I to dehydroacetic acid is achieved in as few as 5 minutes to a yield of up to about 99%. The conversion of compound I to dehydroacetic acid is accompanied by the formation of acetone which is evaporatively removed. When the evolution of acetone ceases the conversion of compound I to dehydroacetic acid is substantially complete.

A solvent or diluent is not required for the success of my process. However, when the process is carried out in the absence of a solvent the crude dehydroacetic acid obtained is typically of lower purity, as represented by the color of the product, than when a solvent is employed (substantially pure dehydroacetic acid being white in color, a less pure product having a light yellow to dark brown color). Therefore, it is preferred that the process be conducted in the presence of an inert solvent. The inert solvent used is a solvent which is substantially unreactive with the starting compound under the conditions of the process. The preferred solvents are dehydroacetic acid and/or an aromatic hydrocarbon such as toluene or xylene (o-, m-, or p- or a mixture thereof). Most preferred of the solvents is dehydroacetic acid. Generally the solvent is employed in about 0.05 to about 2.0 mole per mole of compound I. Larger amounts of solvent of course may be used but it is preferable that the mixture of compound I and solvent be employed in a relatively concentrated form.

As stated above, the crude product ordinarily has a color varying from a light yellow to a dark brown depending on the presence or absence of a solvent as well as on the solvent employed. Purification of the crude product, i.e. decolorization, is readily achieved using conventional purification techniques such as recrystallization or vacuum distillation. The resulting purified product is white in color and has a melting point of 108° C. to 110° C. Both the color and the melting point of the final dehydroacetic acid product meet the specifications required for commercial use.

In a preferred set-up of my invention, 2,2,6-trimethyl-4H-1,3-dioxin-4-one is heated to a temperature of about 130° C. to about 160° C. in the presence of about 0.05 to 2.0 moles of inert solvent, preferably dehydroacetic solvent, per mole of starting compound. The heating is continued until the evolution of acetone ceases. The crude product is then allowed to cool and distilled under reduced pressure to give a white crystalline product in near quantitative yield. It is apparent to those skilled in the art that my invention can readily be conducted as a continuous process as well as a batch process.

The following examples are given to further illustrate the invention, but it is to be understood that the invention is not to be limited in any way by the details described therein.

EXPERIMENTAL EXAMPLE 1 ILLUSTRATING THE PREPARATION OF DEHYDROACETIC ACID IN THE PRESENCE OF XYLENE AS SOLVENT

A solution of 2,2,6-trimethyl-4H-1,3-dioxin-4-one (14.2 g, 0.1 mol) in 20 ml. of mixed xylenes was heated at reflux for 45 minutes. The solvent was removed in vacuo to afford 8.3 g. (99%) of dehydroacetic acid as a light brown solid.

Alternately, the reaction mixture was cooled to 20° C., during which time a golden yellow solid precipitated. Yield 70%, melting point 108°–110° C.

EXPERIMENTAL EXAMPLE 2 ILLUSTRATING THE PREPARATION OF DEHYDROACETIC ACID IN THE PRESENCE OF DEHYDROACETIC ACID AS SOLVENT

Dehydroacetic acid (0.02 mol, 3.4 g.) was heated to 150°±5° C. in a 250-ml. flask under argon atmosphere, and 2,2,6-trimethyl-4H-1,3-dioxin-4-one (0.1 mol, 14.2 g.) was added dropwise over 4 minutes while maintaining the reaction temperature at 150° C. The reaction was heated for an additional 2 minutes, during which time the evolution of acetone ceased. The crude reaction mixture was poured into a Petri dish and immediately solidified into 11.5 g. (97%) of a red solid. This crude product was distilled in a Kugelrohr apparatus (140° C., 5 Torr) to afford white crystals, melting point 109°–111° C. with negligible material loss.

The invention has been described in detail with particular reference to preferred embodiments thereof, but it will be understood that variations and modifications can be effected within the spirit and scope of the invention.

What is claimed is:

1. A process for the preparation of dehydroacetic acid which comprises heating 2,2,6-trimethyl-4H-1,3-dioxin-4-one in the absence of a catalyst and recovering the dehydroacetic acid produced therefrom.

2. A process according to claim 1 wherein the 2,2,6-trimethyl-4H-1,3-dioxin-4-one is heated in the presence of an inert solvent.

3. A process according to claim 2 wherein the solvent is selected from a group consisting of xylene, toluene, and dehydroacetic acid.

4. A process according to claim 2 wherein the solvent is present in an amount of about 0.05 to about 2.0 mole per mole of 2,2,6-trimethyl-4H-1,3-dioxin-4-one.

5. A process according to claim 1 wherein 2,2,6-trimethyl-4H-1,3-dioxin-4-one is heated at a temperature of about 130° C. to about 160° C.

6. A process for the preparation of dehydroacetic acid which comprises heating 2,2,6-trimethyl-4H-1,3-dioxin-4-one at a temperature of about 130° C. to about 160° C. in the absence of a catalyst, in the presence of an inert solvent and recovering the dehydroacetic acid produced therefrom.

7. A process according to claim 6 wherein the 2,2,6-trimethyl-4H-1,3-dioxin-4-one is heated in the presence of dehydroacetic acid as solvent.

8. A process according to claim 6 wherein the solvent is present in an amount of about 0.05 to about 2.0 mole per mole of 2,2,6-trimethyl-4H-1,3-dioxin-4-one.

* * * * *